US007379765B2

(12) United States Patent
Petisce et al.

(10) Patent No.: US 7,379,765 B2
(45) Date of Patent: May 27, 2008

(54) OXYGEN ENHANCING MEMBRANE SYSTEMS FOR IMPLANTABLE DEVICES

(75) Inventors: James Petisce, San Diego, CA (US); Mark A. Tapsak, Orangeville, PA (US); Peter C. Simpson, Del Mar, CA (US); Victoria Carr-Brendel, Pleasanton, CA (US); James H. Brauker, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 10/896,639

(22) Filed: Jul. 21, 2004

(65) Prior Publication Data

US 2005/0054909 A1   Mar. 10, 2005

Related U.S. Application Data

(60) Provisional application No. 60/490,009, filed on Jul. 25, 2003.

(51) Int. Cl.
| | |
|---|---|
| A61B 5/05 | (2006.01) |
| A61B 5/00 | (2006.01) |
| C12M 1/00 | (2006.01) |
| C12N 9/00 | (2006.01) |
| C12N 11/00 | (2006.01) |
| G01N 27/26 | (2006.01) |
| G01N 17/00 | (2006.01) |
| C12Q 1/00 | (2006.01) |
| G01F 1/64 | (2006.01) |

(52) U.S. Cl. .................. 600/345; 600/347; 600/365; 204/403.01; 204/403.03; 204/403.05; 204/403.06; 204/415; 205/778; 205/793

(58) Field of Classification Search ........ 600/345–366, 600/372, 373, 377, 395, 309; 204/403.01–403.14, 204/415; 205/778, 782.5, 783, 937
See application file for complete search history.

(56) References Cited

U.S. PATENT DOCUMENTS 3,979,274 A   9/1976  Newman

| | | |
|---|---|---|
| 4,040,908 A | 8/1977 | Clark, Jr. |
| 4,073,713 A | 2/1978 | Newman |
| 4,260,725 A | 4/1981 | Keogh et al. |
| 4,415,666 A | 11/1983 | D'Orazio et al. |

(Continued)

FOREIGN PATENT DOCUMENTS

EP        0 817 809 B1       1/1998

(Continued)

OTHER PUBLICATIONS

Abstract (English Translation) of JP-2002055076-A, Matsumoto, Tatsu.*

(Continued)

*Primary Examiner*—Charles A. Marmor, II
*Assistant Examiner*—Navin Natnithithadha
(74) *Attorney, Agent, or Firm*—Knobbe Martens Olson & Bear LLP

(57) ABSTRACT

The present invention relates generally to systems and methods for increasing oxygen availability to implantable devices. The preferred embodiments provide a membrane system configured to provide protection of the device from the biological environment and/or a catalyst for enabling an enzymatic reaction, wherein the membrane system includes a polymer formed from a high oxygen soluble material. The high oxygen soluble polymer material is disposed adjacent to an oxygen-utilizing source on the implantable device so as to dynamically retain high oxygen availability to the oxygen-utilizing source during oxygen deficits. Membrane systems of the preferred embodiments are useful for implantable devices with oxygen-utilizing sources and/or that function in low oxygen environments, such as enzyme-based electrochemical sensors and cell transplantation devices.

21 Claims, 5 Drawing Sheets

U.S. PATENT DOCUMENTS

| | | | |
|---|---|---|---|
| 4,418,148 A | | 11/1983 | Oberhardt |
| 4,431,004 A | | 2/1984 | Bessman et al. |
| 4,484,987 A | | 11/1984 | Gough |
| 4,650,547 A | * | 3/1987 | Gough .................. 205/778 |
| 4,680,268 A | | 7/1987 | Clark, Jr. |
| 4,686,044 A | | 8/1987 | Behnke et al. |
| 4,689,309 A | | 8/1987 | Jones |
| 4,703,756 A | | 11/1987 | Gough et al. |
| 4,721,677 A | | 1/1988 | Clark, Jr. |
| 4,803,243 A | | 2/1989 | Fujimoto et al. |
| 4,849,458 A | | 7/1989 | Reed et al. |
| 4,861,830 A | | 8/1989 | Ward, Jr. |
| 4,890,620 A | | 1/1990 | Gough |
| 4,963,595 A | | 10/1990 | Ward et al. |
| 4,970,145 A | * | 11/1990 | Bennetto et al. ........ 204/403.11 |
| 4,994,167 A | | 2/1991 | Shults et al. |
| 5,030,333 A | | 7/1991 | Clark, Jr. |
| 5,140,985 A | | 8/1992 | Schroeder et al. |
| 5,160,418 A | * | 11/1992 | Mullen ................. 204/403.14 |
| 5,235,003 A | | 8/1993 | Ward et al. |
| 5,322,063 A | | 6/1994 | Allen et al. |
| 5,397,848 A | | 3/1995 | Yang et al. |
| 5,428,123 A | | 6/1995 | Ward et al. |
| 5,458,631 A | | 10/1995 | Xavier |
| 5,476,094 A | | 12/1995 | Allen et al. |
| 5,494,562 A | * | 2/1996 | Maley et al. .............. 257/414 |
| 5,589,563 A | | 12/1996 | Ward et al. |
| 5,590,651 A | | 1/1997 | Shaffer et al. |
| 5,605,152 A | | 2/1997 | Slate et al. |
| 5,611,900 A | | 3/1997 | Worden |
| 5,773,270 A | * | 6/1998 | D'Orazio et al. ....... 204/403.01 |
| 5,777,060 A | | 7/1998 | Van Antwerp |
| 5,783,054 A | | 7/1998 | Raguse et al. |
| 5,795,774 A | | 8/1998 | Matsumoto et al. |
| 5,804,048 A | * | 9/1998 | Wong et al. ........... 204/403.09 |
| 5,811,487 A | | 9/1998 | Schulz et al. |
| 5,820,589 A | | 10/1998 | Torgerson et al. |
| 5,882,494 A | * | 3/1999 | Van Antwerp .............. 600/347 |
| 5,964,745 A | | 10/1999 | Lyles et al. |
| 5,964,993 A | | 10/1999 | Blubaugh et al. |
| 5,972,369 A | | 10/1999 | Roorda et al. |
| 5,985,129 A | | 11/1999 | Gough et al. |
| 6,001,067 A | | 12/1999 | Shults et al. |
| 6,015,572 A | | 1/2000 | Lin et al. |
| 6,083,523 A | | 7/2000 | Dionne et al. |
| 6,107,083 A | | 8/2000 | Collins et al. |
| 6,119,028 A | | 9/2000 | Schulman et al. |
| 6,122,536 A | | 9/2000 | Sun et al. |
| 6,141,573 A | | 10/2000 | Kurnik et al. |
| 6,212,416 B1 | | 4/2001 | Ward et al. |
| 6,343,225 B1 | | 1/2002 | Clark, Jr. |
| 6,372,244 B1 | | 4/2002 | Antanavich et al. |
| 6,400,974 B1 | | 6/2002 | Lesho |
| 6,413,396 B1 | | 7/2002 | Yang et al. |
| 6,477,395 B2 | | 11/2002 | Schulman et al. |
| 6,512,939 B1 | | 1/2003 | Colvin et al. |
| 6,514,718 B2 | | 2/2003 | Heller et al. |
| 6,528,584 B2 | | 3/2003 | Kennedy et al. |
| 6,541,107 B1 | | 4/2003 | Zhong et al. |
| 6,545,085 B2 | | 4/2003 | Kilgour et al. |
| 6,551,496 B1 | | 4/2003 | Moles et al. |
| 6,565,509 B1 | | 5/2003 | Say et al. |
| 6,595,919 B2 | | 7/2003 | Berner et al. |
| 6,633,772 B2 | | 10/2003 | Ford et al. |
| 6,702,857 B2 | | 3/2004 | Brauker et al. |
| 6,721,587 B2 | * | 4/2004 | Gough ..................... 600/345 |
| 6,741,877 B1 | | 5/2004 | Shults et al. |
| 6,815,186 B2 | | 11/2004 | Clark, Jr. |
| 6,862,465 B2 | | 3/2005 | Shults et al. |
| 6,973,706 B2 | | 12/2005 | Say et al. |
| 2002/0193885 A1 | | 12/2002 | Legeay et al. |
| 2003/0032874 A1 | | 2/2003 | Rhodes et al. |
| 2003/0059631 A1 | | 3/2003 | Al-Lamee |
| 2003/0065254 A1 | | 4/2003 | Schulman et al. |
| 2005/0027180 A1 | | 2/2005 | Goode et al. |
| 2005/0027181 A1 | | 2/2005 | Goode et al. |
| 2005/0027463 A1 | | 2/2005 | Goode et al. |
| 2005/0031689 A1 | | 2/2005 | Shults et al. |
| 2005/0033132 A1 | | 2/2005 | Shults et al. |
| 2005/0043598 A1 | | 2/2005 | Goode et al. |
| 2005/0051427 A1 | | 3/2005 | Brauker et al. |
| 2005/0051440 A1 | | 3/2005 | Simpson et al. |
| 2005/0056552 A1 | | 3/2005 | Simpson et al. |
| 2005/0090607 A1 | | 4/2005 | Tapsak et al. |
| 2005/0112169 A1 | | 5/2005 | Brauker et al. |
| 2005/0192557 A1 | | 9/2005 | Brauker et al. |
| 2006/0036143 A1 | | 2/2006 | Brister et al. |
| 2006/0159981 A1 | * | 7/2006 | Heller ...................... 429/43 |
| 2006/0258761 A1 | | 11/2006 | Boock et al. |

FOREIGN PATENT DOCUMENTS

| | | | |
|---|---|---|---|
| EP | 0 885 932 A2 | | 12/1998 |
| EP | 1153571 | | 11/2001 |
| GB | 1 442 303 | | 7/1976 |
| JP | 2002055076 A | * | 2/2002 |
| WO | WO 01/20019 A2 | | 3/2001 |
| WO | WO 02/053764 | | 7/2002 |
| WO | WO 2005/044088 A2 | | 5/2005 |

OTHER PUBLICATIONS

Dixon, et al. 2002. Characterization in vitro and in vivo of the oxygen dependence of an enzyme/polymer biosensor for monitoring brain glucose. *Journal of Neuroscience Methods,* 119:135-142.

Gilligan, B. C.; Shults, M.; Rhodes, R. K.; Jacobs, P. G.; Brauker, J. H.; Pintar, T. J.; Updike, S. J. Feasibility of continuo long-term glucose monitoring from a subcutaneous glucose sensor in humans. Diabetes Technol Ther 2004, 6, 378-386.

Heller, A. Implanted electrochemical glucose sensors for the management of diabetes. Annu Rev Biomed Eng 1999. 1, 153-175.

Hitchman, M. L. 1978. "Measurement of Dissolved Oxygen." In Elving, et al. (Eds.). Chemical Analysis, vol. 49, Chap. 3, pp. 34-49, 59-123. New York: John Wiley & Sons.

Kang, S. K.; Jeong, R. A.; Park, S.; Chung, T. D.; Park, S.; Kim, H. C. In vitro and short-term in vivo characteristics of a Kel-F thin film modified glucose sensor. Anal Sci 2003, 19, 1481-1486.

Leypoldt, et al. 1984. Model of a two-substrate enzyme electrode for glucose. *Anal. Chem.,* 56:2896-2904.

Mancy, et al. 1962. A galvanic cell oxygen analyzer. *Journal of Electroanalytical Chemistry,* 4:65-92.

Matsumoto, et al. A long-term lifetime amperometric glucose sensor with a perfluorocarbon polymer coating. Biosens Bioelectron 2001, 16, 271-276.

Myler, et al. Ultra-thin-polysiloxane-film-composite membranes for the optimisation of amperometric oxidase enzyme electrodes. Biosens Bioelectron 2002, 17, 35-43.

Quinn, C. A.; Connor, R. E.; Heller, A. Biocompatible, glucose-permeable hydrogel for in situ coating of implantable biosensors. Biomaterials 1997. 18, 1665-1670.

Rhodes, et al. 1994. Prediction of pocket-portable and implantable glucose enzyme electrode performance from combined species permeability and digital simulation analysis. *Analytical Chemistry,* 66(9):1520-1529.

Schuler, R.; Wittkampf, M.; Chemniti, G. C. Modified gas-permeable silicone rubber membranes for covalent immobilisation of enzymes and their use in biosensor development. Analyst 1999, 124, 1181-1184.

Thomé-Duret, et al. 1996. Modification of the sensitivity of glucose sensor implanted into subcutaneous tissue. *Diabetes Metabolism,* 22:174-178.

Updike, et al. 1982. Implanting the glucose enzyme electrode: Problems, progress, and alternative solutions. *Diabetes Care.* 5(3):207-212.

Ward et al. 2002. A new amperometric glucose microsensor: In vitro and short-term in vivo evaluation. *Biosensors & Bioelectronics,* 17:181-189.

Wientjes, K. J. C. Development of a glucose sensor for diabetic patients. 2000.

Wilkins, E.; Atanasov, P. Glucose monitoring: state of the art and future possibilities. Med Eng Phys 1995, 18, 273-288.

Wilson, et al. 1992. Progress toward the development of an implantable sensor for glucose. *Clin. Chem.,* 38(9):1613-1617.

Wu, et al. 1999. In situ electrochemical oxygen generation with an immunoisolation device. *Ann. N.Y. Acad. Sci.,* 875:105-125.

U.S. Appl. No. 09/447,227, filed Nov. 22, 1999.
U.S. Appl. No. 10/838,658, filed May 3, 2004.
U.S. Appl. No. 10/838,909, filed May 3, 2004.
U.S. Appl. No. 10/838,912, filed May 3, 2004.
U.S. Appl. No. 10/885,476, filed Jul. 6, 2004.
U.S. Appl. No. 10/896,312, filed Jul. 21, 2004.
International Search Report for corresponding PCT application No. PCT/US04/23454, mailed on Oct. 19, 2005.
Written Opinion of International Search Report for corresponding PCT application No. PCT/US04/23454, mailed on Oct. 19, 2005.
U.S. Appl. No. 11/077,715, filed Mar. 10, 2005.
U.S. Appl. No. 11/077,883, filed Mar. 10, 2005.
U.S. Appl. No. 11/077,739, filed Mar. 10, 2005.
U.S. Appl. No. 11/077,740, filed Mar. 10, 2005.
U.S. Appl. No. 11/077,765, filed Mar. 10, 2005.
U.S. Appl. No. 11/078,230, filed Mar. 10, 2005.
U.S. Appl. No. 11/078,232, filed Mar. 10, 2005.
U.S. Appl. No. 11/077,713, filed Mar. 10, 2005.
U.S. Appl. No. 11/077,693, filed Mar. 10, 2005.
U.S. Appl. No. 11/077,714, filed Mar. 10, 2005.
U.S. Appl. No. 11/077,763, filed Mar. 10, 2005.
U.S. Appl. No. 11/077,643, filed Mar. 10, 2005.
U.S. Appl. No. 11/078,072, filed Mar. 10, 2005.
U.S. Appl. No. 11/157,746, filed Jun. 21, 2005.
U.S. Appl. No. 11/157,365, filed Jun. 21, 2005.
U.S. Appl. No. 11/158,227, filed Jun. 21, 2005.
U.S. Appl. No. 11/201,445, filed Aug. 10, 2005.
U.S. Appl. No. 11/055,779, filed Feb. 9, 2005.
International Search Report and Written Opinion received in Appln. No. PCT/US07/03881, mailed Jan. 4, 2008.
Office Action dated Mar. 14, 2007 in U.S. Appl. No. 10/695,636.
Office Action dated May. 22, 2006 in U.S. Appl. No. 10/695,636.
Office Action dated Dec. 6, 2005 in U.S. Appl. No. 10/695,636.

* cited by examiner

FIG. 5A - PRIOR ART

OXYGEN ENHANCING MEMBRANE SYSTEMS FOR IMPLANTABLE DEVICES

RELATED APPLICATION

This application claims the benefit of priority under 35 U.S.C. § 119(e) to U.S. Provisional Application No. 60/490,009, filed Jul. 25, 2003, the contents of which are hereby incorporated by reference in their entirety.

FIELD OF THE INVENTION

The present invention relates generally to systems and methods for increasing oxygen availability in implantable devices.

BACKGROUND OF THE INVENTION

Electrochemical sensors are useful in chemistry and medicine to determine the presence or concentration of a biological analyte. Such sensors are useful, for example, to monitor glucose in diabetic patients and lactate during critical care events.

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) is induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically utilizes uncomfortable finger pricking methods. Due to the lack of comfort and convenience, a diabetic normally only measures his or her glucose level two to four times per day. Unfortunately, these time intervals are spread so far apart that the diabetic likely finds out too late, sometimes incurring dangerous side effects, of a hyperglycemic or hypoglycemic condition. In fact, it is not only unlikely that a diabetic will take a timely SMBG value, but additionally the diabetic will not know if their blood glucose value is going up (higher) or down (lower) based on conventional methods.

Consequently, a variety of transdermal and implantable electrochemical sensors are being developed for continuously detecting and/or quantifying blood glucose values. Many implantable glucose sensors suffer from complications within the body and provide only short-term or less-than-accurate sensing of blood glucose. Similarly, transdermal sensors have problems in accurately sensing and reporting back glucose values continuously over extended periods of time. Some efforts have been made to obtain blood glucose data from implantable devices and retrospectively determine blood glucose trends for analysis; however these efforts do not aid the diabetic in determining real-time blood glucose information. Some efforts have also been made to obtain blood glucose data from transdermal devices for prospective data analysis, however similar problems have been observed.

SUMMARY OF THE PREFERRED EMBODIMENTS

Sensors that can provide accurate, real-time information under ischemic conditions are therefore desirable.

Accordingly, in a first embodiment, an electrochemical sensor for determining a presence or a concentration of an analyte in a fluid is provided, the sensor including a membrane system including an enzyme domain including an enzyme that reacts with the analyte in the fluid as it passes through the enzyme domain; and a working electrode including a conductive material, wherein the working electrode is configured to measure a product of a reaction of the enzyme with the analyte, wherein the membrane system includes a polymer material with a high oxygen solubility.

In an aspect of the first embodiment, the enzyme domain includes a polymer material with a high oxygen solubility.

In an aspect of the first embodiment, the polymer material is selected from the group consisting of silicone, fluorocarbon, and perfluorocarbon.

In an aspect of the first embodiment, the sensor further includes a resistance domain configured to restrict a flow of the analyte therethrough, wherein the resistance domain is located more distal to the working electrode than the enzyme domain, and wherein the resistance domain includes a polymer material with a high oxygen solubility.

In an aspect of the first embodiment, the resistance domain includes a polymer material selected from the group consisting of silicone, fluorocarbon, and perfluorocarbon.

In an aspect of the first embodiment, the sensor further includes a cell impermeable domain that is substantially impermeable to cells, wherein the cell impermeable domain is located more distal to the working electrode than the enzyme domain, and wherein the cell impermeable domain includes a polymer material with a high oxygen solubility.

In an aspect of the first embodiment, the cell impermeable domain includes a polymer material selected from the group consisting of silicone, fluorocarbon, and perfluorocarbon.

In an aspect of the first embodiment, the sensor further includes a cell disruptive domain that includes a substantially porous structure, wherein the cell disruptive domain is located more distal to the working electrode than the enzyme domain, and wherein the cell disruptive domain includes a polymer material with high oxygen solubility.

In an aspect of the first embodiment, the cell impermeable domain includes a polymer material selected from the group consisting of silicone, fluorocarbon, and perfluorocarbon.

In an aspect of the first embodiment, the sensor further includes an interference domain configured to limit or block interfering species, wherein the interference domain is located more proximal to the working electrode than the enzyme domain, and wherein the interference domain includes a polymer material with a high oxygen solubility.

In an aspect of the first embodiment, the interference domain includes a polymer material selected from the group consisting of silicone, fluorocarbon, and perfluorocarbon.

In an aspect of the first embodiment, the sensor further includes an electrolyte domain configured to provide hydrophilicity at the working electrode, wherein the electrolyte domain is located more proximal to the working electrode than the enzyme domain, and wherein the electrolyte domain includes a polymer material with a high oxygen solubility.

In an aspect of the first embodiment, the electrolyte domain includes a polymer material selected from the group consisting of silicone, fluorocarbon, and perfluorocarbon.

In a second embodiment, an analyte sensing device configured for implantation into a tissue of a host is provided, the device including an oxygen-utilizing source; a membrane system configured to provide at least one function selected from the group consisting of protection of the device from a biological environment; diffusion resistance of an analyte; a catalyst for enabling an enzymatic reaction; and limitation of interfering species; wherein the membrane system includes a polymer material with a high oxygen solubility, wherein the membrane system is adjacent to the oxygen-utilizing source.

In an aspect of the second embodiment, the oxygen-utilizing source includes an enzyme.

In an aspect of the second embodiment, the membrane system includes the polymer material with the high oxygen solubility, wherein the polymer material is substantially continuously situated between the enzyme and the tissue.

In an aspect of the second embodiment, the oxygen-utilizing source includes an electroactive surface.

In an aspect of the second embodiment, the membrane system includes the polymer material with the high oxygen solubility, wherein the polymer material is substantially continuously situated between the electroactive surface and the tissue.

In an aspect of the second embodiment, the oxygen-utilizing source includes cells.

In an aspect of the second embodiment, the membrane system includes the polymer material with the high oxygen solubility, wherein the polymer material is substantially continuously situated between the cells and the tissue.

In an aspect of the second embodiment, the polymer material is selected from the group consisting of silicone, fluorocarbon, and perfluorocarbon.

BRIEF DESCRIPTION OF THE DRAWINGS

FIG. 5A is a schematic diagram of oxygen concentration profiles through a prior art membrane.

DETAILED DESCRIPTION OF THE PREFERRED EMBODIMENT

Figure 1:
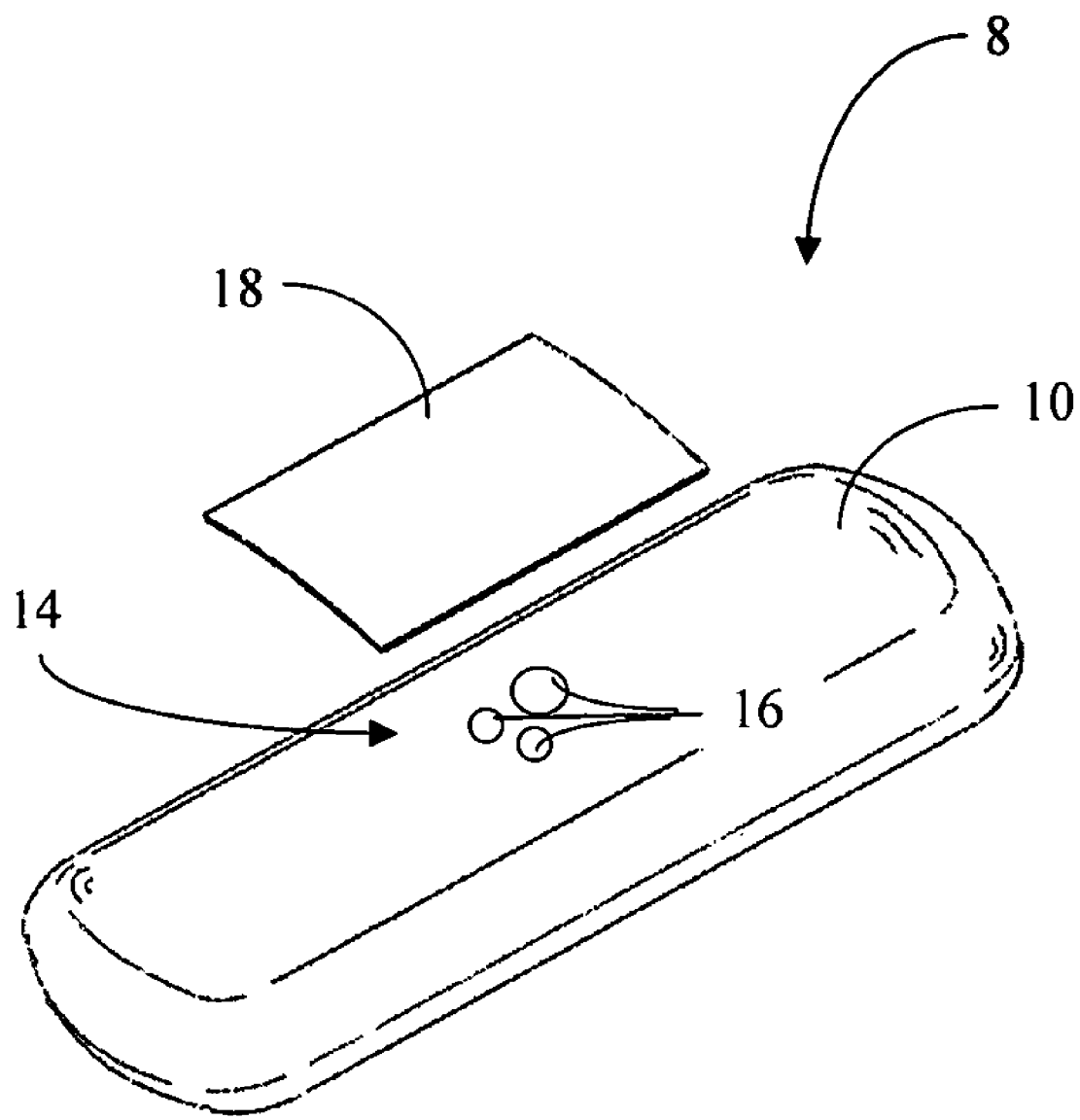
FIG. 1 is an exploded perspective view of an implantable glucose sensor in one exemplary embodiment.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the preferred embodiments, a number of terms are defined below.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcamitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms "operable connection," "operably connected," and "operably linked" as used herein are broad terms and are used in their ordinary sense, including, without limitation, one or more components linked to another component(s) in a manner that allows transmission of signals between the components. For example, one or more electrodes can be used to detect the amount of analyte in a sample and convert that information into a signal; the signal can then be transmitted to a circuit. In this case, the electrode is "operably linked" to the electronic circuitry.

The term "host" as used herein is a broad term and is used in its ordinary sense, including, without limitation, mammals, particularly humans.

The terms "electrochemically reactive surface" and "electroactive surface" as used herein are broad terms and are used in their ordinary sense, including, without limitation, the surface of an electrode where an electrochemical reaction takes place. As one example, a working electrode measures hydrogen peroxide produced by the enzyme catalyzed reaction of the analyte being detected reacts creating an electric current (for example, detection of glucose analyte utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, $O_2$ is reduced at the electrode surface in order to balance the current being generated by the working electrode.

The term "sensing region" as used herein is a broad term and is used in its ordinary sense, including, without limitation, the region of a monitoring device responsible for the detection of a particular analyte. The sensing region generally comprises a non-conductive body, a working electrode, a reference electrode, and/or a counter electrode (optional) passing through and secured within the body forming electrochemically reactive surfaces on the body, an electronic connective means at another location on the body, and a multi-domain membrane affixed to the body and covering the electrochemically reactive surface.

The terms "raw data stream" and "data stream," as used herein, are broad terms and are used in their ordinary sense, including, without limitation, an analog or digital signal directly related to the measured glucose concentration from the glucose sensor. In one example, the raw data stream is digital data in "counts" converted by an A/D converter from an analog signal (for example, voltage or amps) representative of a glucose concentration. The terms broadly encompass a plurality of time spaced data points from a substantially continuous glucose sensor, which comprises individual measurements taken at time intervals ranging from fractions of a second up to, for example, 1, 2, or 5 minutes or longer.

The term "counts," as used herein, is a broad term and is used in its ordinary sense, including, without limitation, a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The term "electrical potential," as used herein, is a broad term and is used in its ordinary sense, including, without limitation, the electrical potential difference between two points in a circuit which is the cause of the flow of a current.

The term "ischemia," as used herein, is a broad term and is used in its ordinary sense, including, without limitation, local and temporary deficiency of blood supply due to obstruction of circulation to a part (for example, sensor). Ischemia can be caused by mechanical obstruction (for example, arterial narrowing or disruption) of the blood supply, for example.

The term "system noise," as used herein, is a broad term and is used in its ordinary sense, including, without limitation, unwanted electronic or diffusion-related noise which can include Gaussian, motion-related, flicker, kinetic, or other white noise, for example.

The terms "signal artifacts" and "transient non-glucose related signal artifacts," as used herein, are broad terms and are used in their ordinary sense, including, without limitation, signal noise that is caused by substantially non-glucose reaction rate-limiting phenomena, such as ischemia, pH changes, temperature changes, pressure, and stress, for example. Signal artifacts, as described herein, are typically transient and are characterized by higher amplitude than system noise.

The terms "low noise," as used herein, is a broad term and is used in its ordinary sense, including, without limitation, noise that substantially decreases signal amplitude.

The terms "high noise" and "high spikes," as used herein, are broad terms and are used in their ordinary sense, including, without limitation, noise that substantially increases signal amplitude.

The term "silicone composition" as used herein is a broad term and is used in its ordinary sense, including, without limitation, a composition of matter that comprises polymers having at least silicon and oxygen atoms in the backbone.

The phrase "distal to" as used herein is a broad term and is used in its ordinary sense, including, without limitation, the spatial relationship between various elements in comparison to a particular point of reference. For example, some embodiments of a device include a membrane system having a cell disruptive domain and a cell impermeable domain. If the sensor is deemed to be the point of reference and the cell disruptive domain is positioned farther from the sensor, then that domain is distal to the sensor.

The phrase "proximal to" as used herein is a broad term and is used in its ordinary sense, including, without limitation, the spatial relationship between various elements in comparison to a particular point of reference. For example, some embodiments of a device include a membrane system having a cell disruptive domain and a cell impermeable domain. If the sensor is deemed to be the point of reference and the cell impermeable domain is positioned nearer to the sensor, then that domain is proximal to the sensor.

The terms "interferants" and "interfering species," as used herein, are broad terms and are used in their ordinary sense, including, but not limited to, effects and/or species that interfere with the measurement of an analyte of interest in a sensor to produce a signal that does not accurately represent the analyte measurement. In an electrochemical sensor, interfering species can include compounds with an oxidation potential that overlaps with that of the analyte to be measured.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview

Membrane systems of the preferred embodiments are suitable for use with implantable devices in contact with a biological fluid. For example, the membrane systems can be utilized with implantable devices such as devices for monitoring and determining analyte levels in a biological fluid, for example, glucose levels for individuals having diabetes. In some embodiments, the analyte-measuring device is a continuous device. Alternatively, the device can analyze a plurality of intermittent biological samples. The analyte-measuring device can use any method of analyte-measurement, including enzymatic, chemical, physical, electrochemical, spectrophotometric, polarimetric, calorimetric, radiometric, or the like.

Although some of the description that follows is directed at glucose-measuring devices, including the described membrane systems and methods for their use, these membrane systems are not limited to use in devices that measure or monitor glucose. These membrane systems are suitable for use in a variety of devices, including, for example, those that detect and quantify other analytes present in biological fluids (including, but not limited to, cholesterol, amino acids, alcohol, galactose, and lactate), cell transplantation devices (see, for example, U.S. Pat. Nos. 6,015,572, 5,964,745, and 6,083,523), drug delivery devices (see, for example, U.S. Pat. Nos. 5,458,631, 5,820,589, and 5,972,369), and the like. Preferably, implantable devices that include the membrane systems of the preferred embodiments are implanted in soft tissue, for example, abdominal, subcutaneous, and peritoneal tissues, the brain, the intramedullary space, and other suitable organs or body tissues.

In addition to the glucose-measuring device described below, the membrane systems of the preferred embodiments can be employed with a variety of known glucose measuring-devices. In some embodiments, the electrode system can be used with any of a variety of known in vivo analyte sensors or monitors, such as U.S. Pat. No. 6,001,067 to Shults et al.; U.S. Pat. No. 6,702,857 to Brauker et al.; U.S. Pat. No. 6,212,416 to Ward et al.; U.S. Pat. No. 6,119,028 to Schulman et al.; U.S. Pat. No. 6,400,974 to Lesho; U.S. Pat. No. 6,595,919 to Berner et al.; U.S. Pat. No. 6,141,573 to Kurnik et al.; U.S. Pat. No. 6,122,536 to Sun et al.; European Patent Application EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al.; U.S. Pat. No. 6,514,718 to Heller et al.; U.S. Pat. No. to 5,985,129 to Gough et al.; WO Patent Application Publication No. 04/021877 to Caduff; U.S. Pat. No. 5,494,562 to Maley et al.; U.S. Pat. No. 6,120,676 to Heller et al.; and U.S. Pat. No. 6,542,765 to Guy et al, each of which are incorporated in there entirety herein by reference. In general, it is understood that the disclosed embodiments are applicable to a variety of continuous glucose measuring device configurations.

FIG. 1 is an exploded perspective view of one exemplary embodiment comprising an implantable glucose sensor 10 that utilizes amperometric electrochemical sensor technology to measure glucose. In this exemplary embodiment, a body 12 with a sensing region 14 includes an electrode system 16 and sensor electronics, which are described in more detail with reference to FIG. 2.

In this embodiment, the electrode system 16 is operably connected to the sensor electronics (FIG. 2) and includes electroactive surfaces, which are covered by a membrane system 18. The membrane system 18 is disposed over the electroactive surfaces of the electrode system 16 and provides one or more of the following functions: 1) protection of the exposed electrode surface from the biological environment (cell impermeable domain); 2) diffusion resistance (limitation) of the analyte (resistance domain); 3) a catalyst for enabling an enzymatic reaction (enzyme domain); 4) limitation or blocking of interfering species (interference domain); and/or 5) hydrophilicity at the electrochemically reactive surfaces of the sensor interface (electrolyte domain), for example, as described in co-pending U.S. patent application Ser. No. 10/838,912, filed May 3, 2004 and entitled "IMPLANTABLE ANALYTE SENSOR," the contents of which are hereby incorporated herein by reference in their entirety. The membrane system can be attached to the sensor body 12 by mechanical or chemical methods such as are described in co-pending U.S. Patent Application MEMBRANE ATTACHMENT and U.S. patent application Ser. No. 10/838,912 filed May 3, 2004 and entitled, "IMPLANTABLE ANALYTE SENSOR", the contents of which are hereby incorporated herein by reference in their entirety.

Figure 3:
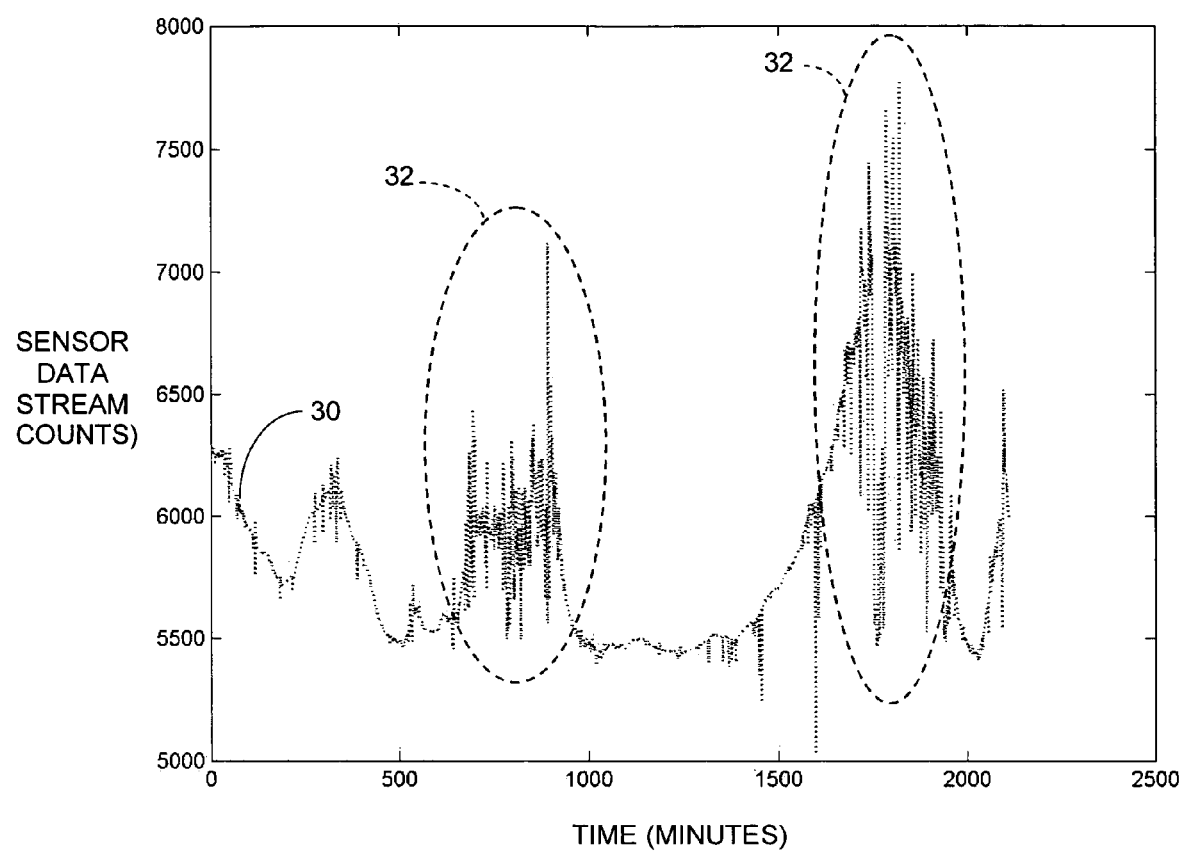
FIG. 3 is a graph that shows a raw data stream obtained from a glucose sensor over a 36-hour time span in one example.
Figure 4:
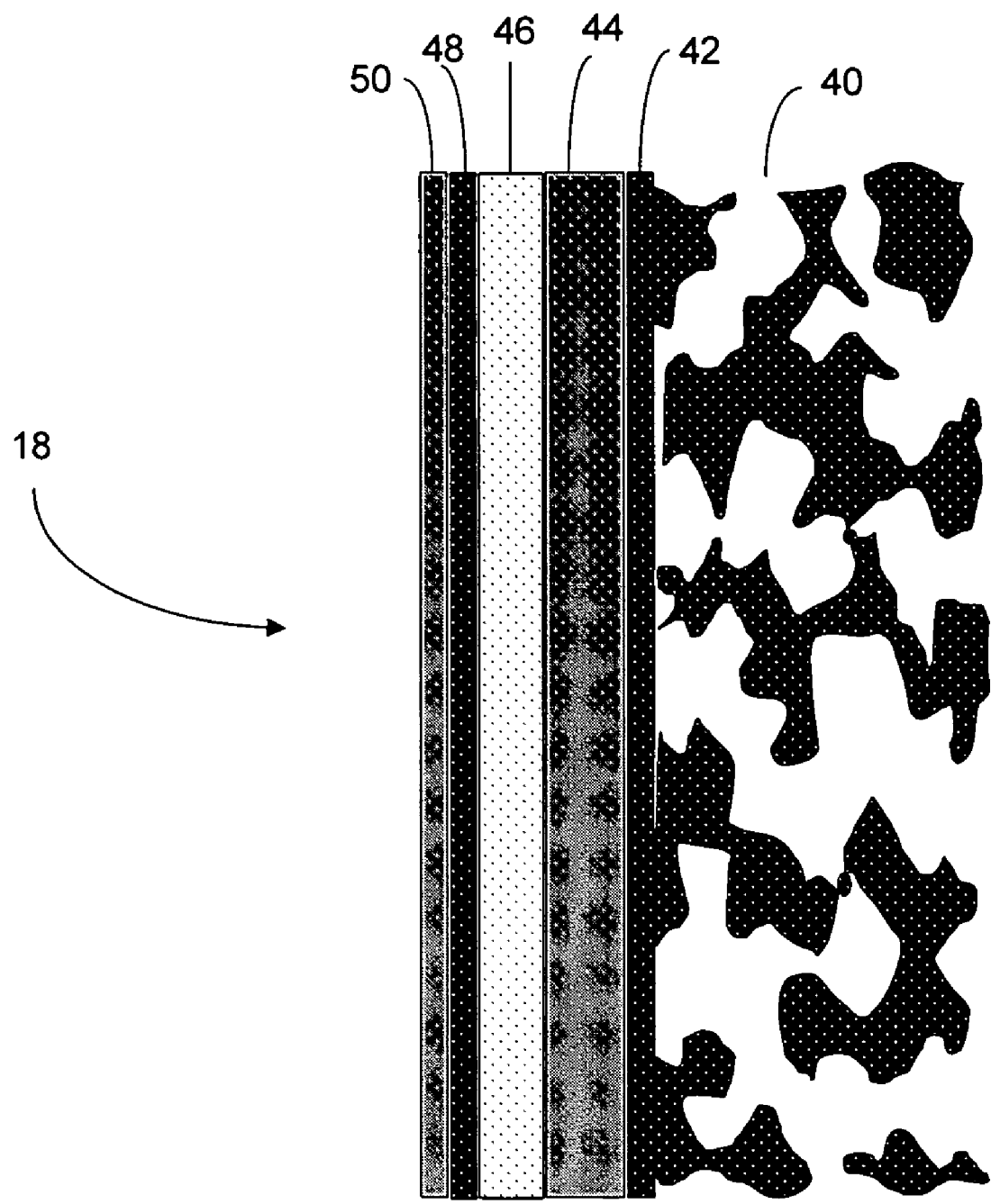
FIG. 4 is a schematic illustration of a membrane system of the device of FIG. 1.
Figure 5B:
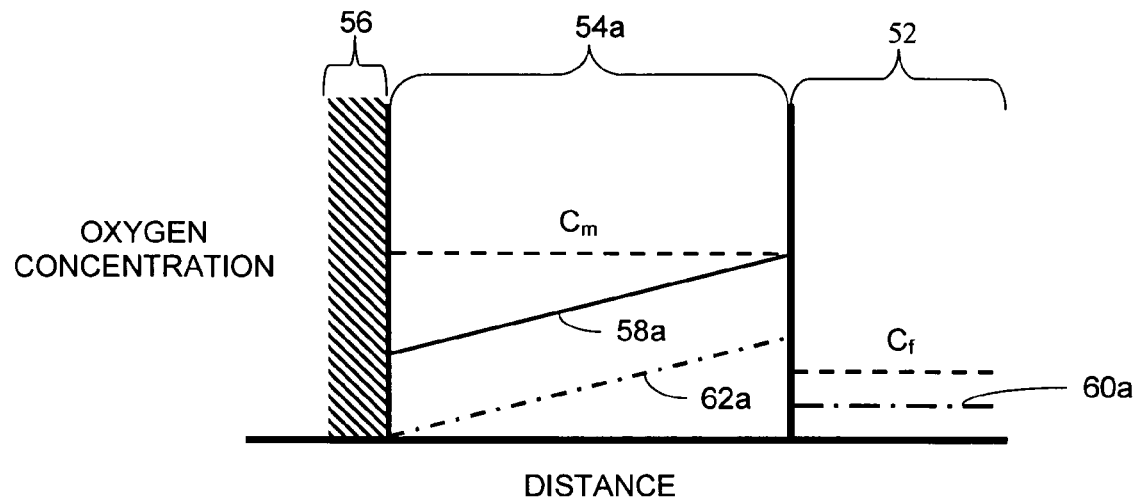
FIG. 5B is a schematic diagram of oxygen concentration profiles through the membrane system of the preferred embodiments.
Figure 5B:
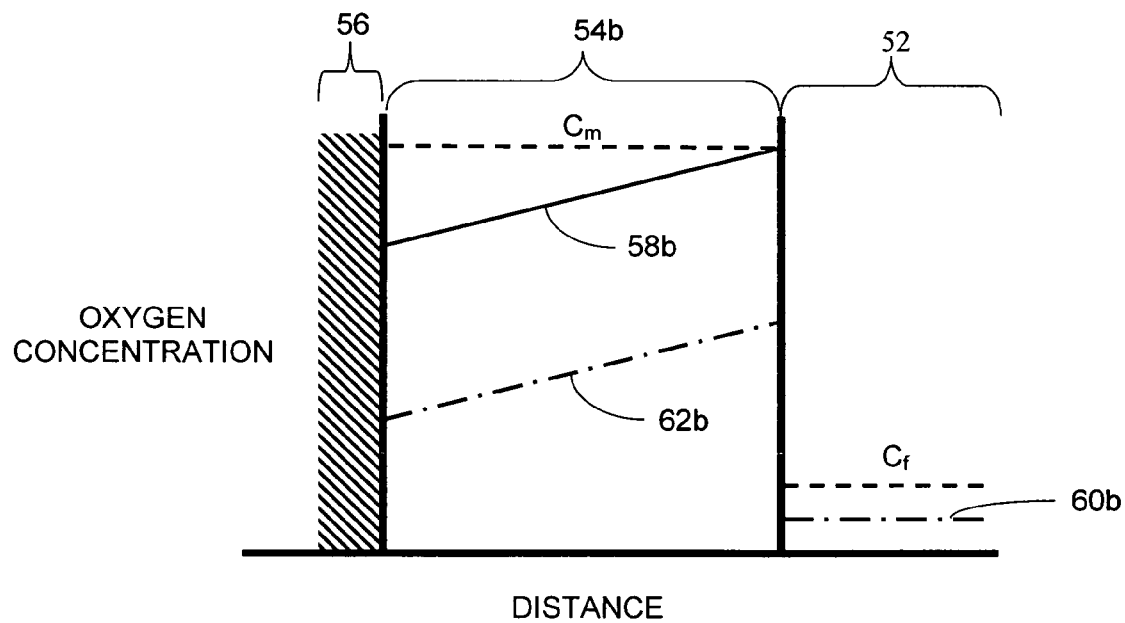

The membrane system 18 of the preferred embodiments, which are described in more detail below with reference to FIGS. 4 and 5, is formed at least partially from materials with high oxygen solubility. These materials act as a high oxygen soluble domain, dynamically retaining a high availability of oxygen that can be used to compensate for the local oxygen deficit during times of transient ischemia, which is described in more detail below and with reference to FIG. 3. As a result, the membrane systems of the preferred embodiments enable glucose sensors and other implantable devices such as cell transplantation devices to function in the subcutaneous space even during local transient ischemia.

In some embodiments, the electrode system 16, which is located on or within the sensing region 14, is comprised of at least a working and a reference electrode with an insulating material disposed therebetween. In some alternative embodiments, additional electrodes can be included within the electrode system, for example, a three-electrode system (working, reference, and counter electrodes) and/or including an additional working electrode (which can be used to generate oxygen, measure an additional analyte, or can be configured as a baseline subtracting electrode, for example).

In the exemplary embodiment of FIG. 1, the electrode system includes three electrodes (working, counter, and reference electrodes), wherein the counter electrode is provided to balance the current generated by the species being measured at the working electrode. In the case of a glucose oxidase based glucose sensor, the species being measured at the working electrode is $H_2O_2$. Glucose oxidase, GOX, catalyzes the conversion of oxygen and glucose to hydrogen peroxide and gluconate according to the following reaction:

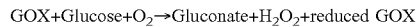

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons (2H+), two electrons (2e−), and one oxygen molecule (O2). In such embodiments, because the counter electrode utilizes oxygen as an electron acceptor, the most likely reducible species for this system are oxygen or enzyme generated peroxide. There are two main pathways by which oxygen can be consumed at the counter electrode. These pathways include a four-electron pathway to produce hydroxide and a two-electron pathway to produce hydrogen peroxide. In addition to the counter electrode, oxygen is further consumed by the reduced glucose oxidase within the enzyme domain. Therefore, due to the oxygen consumption by both the enzyme and the counter electrode, there is a net consumption of oxygen within the electrode system. Theoretically, in the domain of the working electrode there is significantly less net loss of oxygen than in the region of the counter electrode. In addition, there is a close correlation between the ability of the counter electrode to maintain current balance and sensor function.

In general, in electrochemical sensors wherein an enzymatic reaction depends on oxygen as a co-reactant, depressed function or inaccuracy can be experienced in low oxygen environments, for example in vivo. Subcutaneously implanted devices are especially susceptible to transient ischemia that can compromise device function; for example, because of the enzymatic reaction required for an implantable amperometric glucose sensor, oxygen must be in excess over glucose in order for the sensor to effectively function as a glucose sensor. If glucose becomes in excess, the sensor turns into an oxygen sensitive device. In vivo, glucose concentration can vary from about one hundred times or more that of the oxygen concentration. Consequently, oxygen becomes a limiting reactant in the electrochemical reaction and when insufficient oxygen is provided to the sensor, the sensor is unable to accurately measure glucose concentration. Those skilled in the art interpret oxygen limitations resulting in depressed function or inaccuracy as a problem of availability of oxygen to the enzyme and/or counter electrode. Oxygen limitations can also be seen during periods of transient ischemia that occur, for example, under certain postures or when the region around the implanted sensor is compressed so that blood is forced out of the capillaries. Such ischemic periods observed in implanted sensors can last for many minutes or even an hour or longer.

Figure 2:
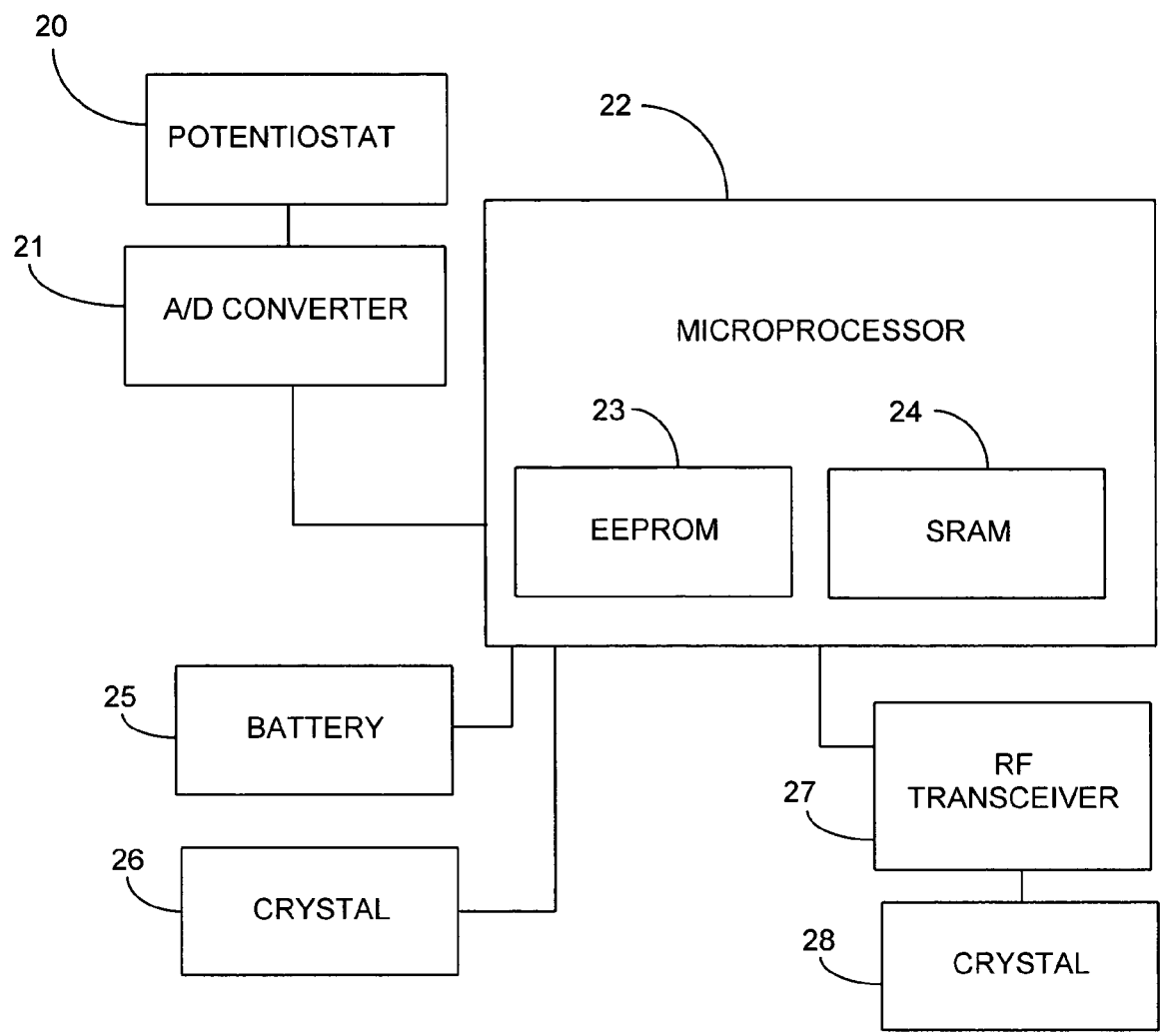
FIG. 2 is a block diagram that illustrates the sensor electronics in one embodiment; however a variety of sensor electronics configurations can be implemented with the preferred embodiments.

FIG. 2 is a block diagram that illustrates sensor electronics in one exemplary embodiment; one skilled in the art appreciates, however, a variety of sensor electronics configurations can be implemented with the preferred embodiments. In this embodiment, a potentiostat 20 is shown, which is operatively connected to electrode system 16 (FIG. 1) to obtain a current value, and includes a resistor (not shown) that translates the current into voltage. The A/D converter 21 digitizes the analog signal into "counts" for processing. Accordingly, the resulting raw data signal in counts is directly related to the current measured by the potentiostat.

A microprocessor 22 is the central control unit that houses EEPROM 23 and SRAM 24, and controls the processing of the sensor electronics. The alternative embodiments can utilize a computer system other than a microprocessor to process data as described herein. In some alternative embodiments, an application-specific integrated circuit (ASIC) can be used for some or all the sensor's central processing. EEPROM 23 provides semi-permanent storage of data, storing data such as sensor ID and programming to process data signals (for example, programming for data smoothing such as described elsewhere herein). SRAM 24 is used for the system's cache memory, for example for temporarily storing recent sensor data.

The battery 25 is operatively connected to the microprocessor 22 and provides the power for the sensor. In one embodiment, the battery is a Lithium Manganese Dioxide battery, however any appropriately sized and powered battery can be used. In some embodiments, a plurality of batteries can be used to power the system. Quartz Crystal 26 is operatively connected to the microprocessor 22 and maintains system time for the computer system.

The RF Transceiver 27 is operably connected to the microprocessor 22 and transmits the sensor data from the sensor to a receiver. Although a RF transceiver is shown here, some other embodiments can include a wired rather than wireless connection to the receiver. In yet other embodiments, the sensor can be transcutaneously connected via an inductive coupling, for example. The quartz crystal 28 provides the system time for synchronizing the data transmissions from the RF transceiver. The transceiver 27 can be substituted with a transmitter in one embodiment.

Although FIGS. 1 to 2 and associated text illustrate and describe one exemplary embodiment of an implantable glucose sensor, the electrode system, electronics and its method of manufacture of the preferred embodiments described below can be implemented on any known electrochemical sensor, including those described in co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; "OPTIMIZED SENSOR GEOMETRY FOR AN IMPLANTABLE GLUCOSE SENSOR"; U.S. application Ser. No. 10/633,367 filed Aug. 1, 2003 entitled, "SYSTEM AND METHODS FOR PROCESSING ANALYTE SENSOR DATA", the contents of each of which are hereby incorporated by reference in their entireties.

FIG. 3 is a graph that shows a raw data stream obtained from a glucose sensor with a conventional membrane system. The x-axis represents time in minutes. The y-axis represents sensor data in counts. In this example, sensor output in counts is transmitted every 30 seconds. The raw data stream 30 includes substantially smooth sensor output in some portions, however other portions exhibit transient non-glucose related signal artifacts 32.

The raw data stream 30 includes substantially smooth sensor output in some portions, however other portions exhibit erroneous or transient non-glucose related signal artifacts 32. Particularly, referring to the signal artifacts 32, it is believed that effects of local ischemia on prior art electrochemical sensors creates erroneous (non-glucose) signal values due to oxygen deficiencies either at the enzyme within the membrane system and/or at the counter electrode on the electrode surface.

In one situation, when oxygen is deficient relative to the amount of glucose, the enzymatic reaction is limited by oxygen rather than glucose. Thus, the output signal is indicative of the oxygen concentration rather than the glucose concentration, producing erroneous signals. Additionally, when an enzymatic reaction is rate-limited by oxygen, glucose is expected to build up in the membrane because it is not completely catabolized during the oxygen deficit. When oxygen is again in excess, there is also excess glucose due to the transient oxygen deficit. The enzyme rate then speeds up for a short period until the excess glucose is catabolized, resulting in spikes of non-glucose related increased sensor output. Accordingly, because excess oxygen (relative to glucose) is necessary for proper sensor function, transient ischemia can result in a loss of signal gain in the sensor data.

In another situation, oxygen deficiency can be seen at the counter electrode when insufficient oxygen is available for reduction, which thus affects the counter electrode in that it is unable to balance the current coming from the working electrode. When insufficient oxygen is available for the counter electrode, the counter electrode can be driven in its electrochemical search for electrons all the way to its most negative value, which can be ground, or 0.0 V, which causes the reference to shift, reducing the bias voltage such as is described in more detail below. In other words, a common result of ischemia is seen as a drop off in sensor current as a function of glucose concentration (for example, lower sensitivity). This occurs because the working electrode no longer oxidizes all of the $H_2O_2$ arriving at its surface because of the reduced bias. In some extreme circumstances, an increase in glucose can produce no increase in current or even a decrease in current.

In some situations, transient ischemia can occur at high glucose levels, wherein oxygen can become limiting to the enzymatic reaction, resulting in a non-glucose dependent downward trend in the data. In some situations, certain movements or postures taken by the patient can cause transient signal artifacts as blood is squeezed out of the capillaries, resulting in local ischemia, and causing non-glucose dependent signal artifacts. In some situations, oxygen can also become transiently limited due to contracture of tissues around the sensor interface. This is similar to the blanching of skin that can be observed when one puts pressure on it. Under such pressure, transient ischemia can occur in both the epidermis and subcutaneous tissue. Transient ischemia is common and well tolerated by subcutaneous tissue. However, such ischemic periods can cause an oxygen deficit in implanted devices that can last for many minutes or even an hour or longer.

Although some examples of the effects of transient ischemia on a prior art glucose sensor are described above, similar effects can be seen with analyte sensors that use alternative catalysts to detect other analytes, for example, amino acids (amino acid oxidase), alcohol (alcohol oxidase), galactose (galactose oxidase), lactate (lactate oxidase), and cholesterol (cholesterol oxidase), or the like.

Membrane Systems of the Preferred Embodiments

In order to overcome the effects of transient ischemia, the membrane systems 18 of the preferred embodiments include materials with high oxygen solubility. These materials increase the local amount of oxygen to aid in compensating for local oxygen deficits during ischemic conditions. As a result, the membrane systems of the preferred embodiments enable analyte sensors and other devices such as cell transplantation devices to function in the subcutaneous space even during local transient ischemia.

The phrases "high oxygen solubility" and "high oxygen soluble" as used herein are broad phrases and are used in their ordinary sense, including, without limitation, a domain or material property that includes higher oxygen solubility than aqueous media so that it concentrates oxygen from the biological fluid surrounding the membrane system. In some preferred embodiments, a high oxygen solubility polymer has at least about 3× higher oxygen solubility than aqueous media, more preferably at least about 4×, 5×, or 6× higher oxygen solubility than aqueous media, and most preferably at least about 7×, 8×, 9×, 10× or more higher oxygen solubility than aqueous media. In one embodiment, high oxygen solubility is defined as having higher oxygen solubility than at least one of a hydrocarbonaceous polymer and an oxyhydrocarbon polymer (a hydrocarbonaceous polymer is a polymeric material consisting of carbon and hydrogen atoms and an oxyhydrocarbonaceous polymer is a polymeric material consisting of carbon, hydrogen, and oxygen atoms). Oxygen solubility can be measured using any known technique, for example by removing the oxygen from the polymer (namely, solution) via at least three Freeze-Pump-Thaw cycles and then measuring the resultant oxygen (for example, using a manometer).

Oxygen permeability (Dk) is calculated as diffusion multiplied by solubility. Oxygen Permeability is conveniently reported in units of Barrers (1 Barrer=$10^{-10}$ $cm^3$ $O_2$ (STP) $cm/cm^2 s$ cmHg). Insulating materials of preferred embodiments that have a high oxygen permeability typically have an oxygen permeability of from about 1 Barrer or less to about 1000 Barrers or more, preferably from about 1, 2, 3, 4, 5, 6, 7, 8, 9, 10, 15, 20, 25, 30, 35, 40, 45, 50, 55, 60, 65, 70, 75, 80, 85, 90, 95, or 100 Barrers to about 125, 150, 175, 200, 225, 250, 275, 300, 325, 350, 375, 400, 425, 450, 475, 500, 550, 600, 650, 700, 750, 800, 850, 900, or 950 Barrers.

In one exemplary embodiment, the properties of silicone (and/or silicone compositions) inherently enable materials formed from silicone to act as a high oxygen solubility domain. Utilization of a high oxygen soluble material in an electrochemical sensor is advantageous because it is believed to dynamically retain high oxygen availability to oxygen-utilizing sources (for example, an enzyme and/or a counter electrode of an electrochemical cell).

As described below with reference to FIG. 4, the membrane system 18 can include two or more domains that cover an implantable device, for example, an implantable glucose sensor. In the example of an implantable enzyme-based electrochemical glucose sensor, the membrane prevents direct contact of the biological fluid sample with the electrodes, while controlling the permeability of selected substances (for example, oxygen and glucose) present in the biological fluid through the membrane for reaction in an enzyme rich domain with subsequent electrochemical reaction of formed products at the electrodes.

The membrane systems of preferred embodiments are constructed of two or more domains. The multi-domain membrane can be formed from one or more distinct layers and can comprise the same or different materials. The term "domain" is a broad term and is used in its ordinary sense, including, without limitation, a single homogeneous layer or region that incorporates the combined functions one or more domains, or a plurality of layers or regions that each provide one or more of the functions of each of the various domains.

FIG. 4 is an illustration of a membrane system in one preferred embodiment. The membrane system 18 can be used with a glucose sensor such, as is described above with reference to FIG. 1. In this embodiment, the membrane system 18 includes a cell disruptive domain 40 most distal of all domains from the electrochemically reactive surfaces, a cell impermeable domain 42 less distal from the electrochemically reactive surfaces than the cell disruptive domain, a resistance domain 44 less distal from the electrochemically reactive surfaces than the cell impermeable domain, an enzyme domain 46 less distal from the electrochemically reactive surfaces than the resistance domain, an interference domain 48 less distal from the electrochemically reactive surfaces than the enzyme domain, and an electrolyte domain 50 adjacent to the electrochemically reactive surfaces. However, it is understood that the membrane system can be modified for use in other devices, by including only two or more of the domains, or additional domains not recited above.

In some embodiments, the membrane system is formed as a homogeneous membrane, namely, a membrane having substantially uniform characteristics from one side of the membrane to the other. However, a membrane can have heterogeneous structural domains, for example, domains resulting from the use of block copolymers (for example, polymers in which different blocks of identical monomer units alternate with each other), but can be defined as homogeneous overall in that each of the above-described domains functions by the preferential diffusion of some substance through the homogeneous membrane.

In the preferred embodiments, one or more of the above-described domains are formed from high oxygen solubility material. Utilization of high oxygen solubility material is advantageous because it is believed to dynamically retain a higher amount of oxygen, which maintains higher oxygen availability to selected locations (for example, the enzyme and/or counter electrode). In some embodiments, the high oxygen soluble material includes silicones, fluorocarbons, perfluorocarbons, or the like. In one embodiment, one or more domains is/are formed from a silicone composition that allows the transport of glucose other such water-soluble molecules (for example, drugs), such as are described in more detail with reference to co-pending U.S. application Ser. No. 10/695,636 filed Oct. 28, 2003 and published as U.S. Application Publication No. 2005-0090607 and entitled, "SILICONE COMPOSITION FOR BIOCOMPATIBLE MEMBRANE," the contents of which are hereby incorporated by reference in their entireties.

Cell Disruptive Domain

The cell disruptive domain 40 is positioned most distal to the implantable device and is designed to support tissue ingrowth, to disrupt contractile forces typically found in a foreign body capsule, to encourage vascularity within the membrane, and/or to disrupt the formation of a barrier cell layer. In one embodiment, the cell disruptive domain 40 has an open-celled configuration with interconnected cavities and solid portions, wherein the distribution of the solid portion and cavities of the cell disruptive domain includes a substantially co-continuous solid domain and includes more than one cavity in three dimensions substantially throughout the entirety of the first domain. Cells can enter into the cavities; however they cannot travel through or wholly exist within the solid portions. The cavities allow most substances to pass through, including, for example, cells and molecules. U.S. Pat. No. 6,702,857, filed Jul. 27, 2001, and entitled "MEMBRANE FOR USE WITH IMPLANTABLE DEVICES" and U.S. patent application Ser. No. 10/647,065, filed Aug. 22, 2003, and entitled, "POROUS MEMBRANES FOR USE WITH IMPLANTABLE DEVICES" describe membranes having a cell disruptive domain.

The cell disruptive domain 40 is preferably formed from high oxygen soluble materials such as polymers formed from silicone, fluorocarbons, perfluorocarbons, or the like. In one embodiment, the cell disruptive domain is formed from a silicone composition with a non-silicon containing hydrophile such as such as polyethylene glycol, propylene glycol, pyrrolidone, esters, amides, carbonates, or polypropylene glycol covalently incorporated or grafted therein. In some alternative embodiments, the cell disruptive domain is formed from polyethylene-co-tetrafluoroethylene, polyolefin, polyester, polycarbonate, biostable polytetrafluoroethylene, homopolymers, copolymers, terpolymers of polytetrafluoroethylene, polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones or block copolymers thereof including, for example, di-block, tri-block, alternating, random and graft copolymers.

In preferred embodiments, the thickness of the cell disruptive domain is from about 10 or less, 20, 30, 40, 50, 60, 70, 80, or 90 microns to about 1500, 2000, 2500, or 3000 or more microns. In more preferred embodiments, the thickness of the cell disruptive domain is from about 100, 150, 200 or 250 microns to about 1000, 1100, 1200, 1300, or 1400 microns. In even more preferred embodiments, the thickness of the cell disruptive domain is from about 300, 350, 400, 450, 500, or 550 microns to about 500, 550, 600, 650, 700, 750, 800, 850, or 900 microns.

The cell disruptive domain is optional and can be omitted when using an implantable device that does not prefer tissue ingrowth, for example, a short-lived device (for example, less than one day to about a week) or one that delivers tissue response modifiers.

Cell Impermeable Domain

The cell impermeable domain 42 is positioned less distal to the implantable device than the cell disruptive domain, and can be resistant to cellular attachment, impermeable to cells, and/or is composed of a biostable material. When the cell impermeable domain is resistant to cellular attachment (for example, attachment by inflammatory cells, such as macrophages, which are therefore kept a sufficient distance from other domains, for example, the enzyme domain), hypochlorite and other oxidizing species are short-lived chemical species in vivo, and biodegradation does not occur. Additionally, the materials preferred for forming this domain are resistant to the effects of these oxidative species and have thus been termed biodurable. See, for example, U.S. Pat. No. 6,702,857, filed Jul. 27, 2001, and entitled "MEMBRANE FOR USE WITH IMPLANTABLE DEVICES" and U.S. patent application Ser. No. 10/647,065, filed Aug. 22, 2003, and entitled, "POROUS MEMBRANES FOR USE WITH IMPLANTABLE DEVICES."

The cell impermeable domain 42 is preferably formed from high oxygen soluble materials such as polymers formed from silicone, fluorocarbons, perfluorocarbons, or the like. In one embodiment, the cell impermeable domain is formed from a silicone composition with a hydrophile such as such as polyethylene glycol, propylene glycol, pyrrolidone, esters, amides, carbonates, or polypropylene glycol covalently incorporated or grafted therein. In some alternative embodiments, the cell impermeable domain is formed from copolymers or blends of copolymers with hydrophilic polymers such as polyvinylpyrrolidone (PVP), polyhydroxyethyl methacrylate, polyvinylalcohol, polyacrylic acid, polyethers such as polyethylene glycol, and block copolymers thereof, including, for example, di-block, tri-block, alternating, random and graft copolymers (block copolymers are discussed in U.S. Pat. Nos. 4,803,243 and 4,686,044).

In preferred embodiments, the thickness of the cell impermeable domain is from about 10 or 15 microns or less to about 125, 150, 175, or 200 microns or more. In more preferred embodiments, the thickness of the cell impermeable domain is from about 20, 25, 30, or 35 microns to about 65, 70, 75, 80, 85, 90, 95, or 100 microns. In even more preferred embodiments, the cell impermeable domain is from about 40 or 45 microns to about 50, 55, or 60 microns thick.

The cell disruptive domain 40 and cell impermeable domain 42 of the membrane system can be formed together as one unitary structure. Alternatively, the cell disruptive and cell impermeable domains 40, 42 of the membrane system can be formed as two layers mechanically or chemically bonded together.

Resistance Domain

The resistance domain 44 is situated more proximal to the implantable device relative to the cell disruptive domain. The resistance domain controls the flux of oxygen and other analytes (for example, glucose) to the underlying enzyme domain. As described in more detail elsewhere herein, there exists a molar excess of glucose relative to the amount of oxygen in blood; that is, for every free oxygen molecule in extracellular fluid, there are typically more than 100 glucose molecules present (see Updike et al., Diabetes Care 5:207-21(1982)). However, an immobilized enzyme-based sensor employing oxygen as cofactor is supplied with oxygen in non-rate-limiting excess in order to respond linearly to changes in glucose concentration, while not responding to changes in oxygen tension. More specifically, when a glucose-monitoring reaction is oxygen-limited, linearity is not achieved above minimal concentrations of glucose. Without a semipermeable membrane situated over the enzyme domain to control the flux of glucose and oxygen, a linear response to glucose levels can be obtained only up to about 40 mg/dL. However, in a clinical setting, a linear response to glucose levels is desirable up to at least about 500 mg/dL.

The resistance domain 44 includes a semipermeable membrane that controls the flux of oxygen and glucose to the underlying enzyme domain 46, preferably rendering oxygen in non-rate-limiting excess. As a result, the upper limit of linearity of glucose measurement is extended to a much higher value than that which is achieved without the resistance domain. In one embodiment, the resistance domain 44 exhibits an oxygen-to-glucose permeability ratio of approximately 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)). In some embodiments, a lower ratio of oxygen-to-glucose can be sufficient to provide excess oxygen by using a high oxygen soluble domain (for example, a silicone material) to enhance the supply/transport of oxygen to the enzyme membrane and/or electroactive surfaces. By enhancing the oxygen supply through the use of a silicone composition, for example, glucose concentration can be less of a limiting factor. In other words, if more oxygen is supplied to the enzyme and/or electroactive surfaces, then more glucose can also be supplied to the enzyme without creating an oxygen rate-limiting excess.

The resistance domain 44 is preferably formed from high oxygen soluble materials such as polymers formed from silicone, fluorocarbons, perfluorocarbons, or the like. In one embodiment, the resistance domain is formed from a silicone composition with a hydrophile such as such as polyethylene glycol, propylene glycol, pyrrolidone, esters, amides, carbonates, or polypropylene glycol covalently incorporated or grafted therein. In some alternative embodiments, the resistance domain is from polyurethane, for example, a polyurethane urea/polyurethane-block-polyethylene glycol blend.

In some embodiments, the resistance domain 44 can be formed as a unitary structure with the cell impermeable domain 42; that is, the inherent properties of the resistance domain 44 can provide the functionality described with reference to the cell impermeable domain 42 such that the cell impermeable domain 42 is incorporated as a part of resistance domain 44. In these embodiments, the combined resistance domain/cell impermeable domain can be bonded to or formed as a skin on the cell disruptive domain 40 during a molding process such as described above. In another embodiment, the resistance domain 44 is formed as a distinct layer and chemically or mechanically bonded to the cell disruptive domain 40 (if applicable) or the cell impermeable domain 42 (when the resistance domain is distinct from the cell impermeable domain).

In preferred embodiments, the thickness of the resistance domain is from about 10 microns or less to about 200 microns or more. In more preferred embodiments, the thickness of the resistance domain is from about 15, 20, 25, 30, or 35 microns to about 65, 70, 75, 80, 85, 90, 95, or 100 microns. In more preferred embodiments, the thickness of the resistance domain is from about 40 or 45 microns to about 50, 55, or 60 microns.

Enzyme Domain

An immobilized enzyme domain 46 is situated less distal from the electrochemically reactive surfaces than the resistance domain 44. In one embodiment, the immobilized enzyme domain 46 comprises glucose oxidase. In other embodiments, the immobilized enzyme domain 46 can be impregnated with other oxidases, for example, galactose oxidase, cholesterol oxidase, amino acid oxidase, alcohol oxidase, lactate oxidase, or uricase. For example, for an enzyme-based electrochemical glucose sensor to perform well, the sensor's response should neither be limited by enzyme activity nor cofactor concentration.

The enzyme domain 44 is preferably formed from high oxygen soluble materials such as polymers formed from silicone, fluorocarbons, perfluorocarbons, or the like. In one embodiment, the enzyme domain is formed from a silicone composition with a hydrophile such as such as polyethylene glycol, propylene glycol, pyrrolidone, esters, amides, carbonates, or polypropylene glycol covalently incorporated or grafted therein.

In one preferred embodiment, high oxygen solubility within the enzyme domain can be achieved by using a polymer matrix to host the enzyme within the enzyme domain, which has a high solubility of oxygen. In one exemplary embodiment of fluorocarbon-based polymers, the solubility of oxygen within a perfluorocarbon-based polymer is 50-volume %. As a reference, the solubility of oxygen in water is approximately 2-volume %.

Utilization of a high oxygen solubility material for the enzyme domain is advantageous because the oxygen dissolves more readily within the domain and thereby acts as a high oxygen soluble domain optimizing oxygen availability to oxygen-utilizing sources (for example, the enzyme and/or counter electrode). When the resistance domain 44 and enzyme domain 46 both comprise a high oxygen soluble material, the chemical bond between the enzyme domain 46 and resistance domain 44 can be optimized, and the manufacturing made easy.

In preferred embodiments, the thickness of the enzyme domain is from about 1 micron or less to about 40, 50, 60, 70, 80, 90, or 100 microns or more. In more preferred embodiments, the thickness of the enzyme domain is between about 1, 2, 3, 4, or 5 microns and 13, 14, 15, 20, 25, or 30 microns. In even more preferred embodiments, the thickness of the enzyme domain is from about 6, 7, or 8 microns to about 9, 10, 11, or 12 microns.

Interference Domain

The interference domain 48 is situated less distal to the implantable device than the immobilized enzyme domain. Interferants are molecules or other species that are electro-reduced or electro-oxidized at the electrochemically reactive surfaces, either directly or via an electron transfer agent, to produce a false signal (for example, urate, ascorbate, or acetaminophen). In one embodiment, the interference domain 48 prevents the penetration of one or more interferants into the electrolyte phase around the electrochemically reactive surfaces. Preferably, this type of interference domain is much less permeable to one or more of the interferants than to the analyte.

In one embodiment, the interference domain 48 can include ionic components incorporated into a polymeric matrix to reduce the permeability of the interference domain to ionic interferants having the same charge as the ionic components. In another embodiment, the interference domain 48 includes a catalyst (for example, peroxidase) for catalyzing a reaction that removes interferants. U.S. Pat. Nos. 6,413,396 and 6,565,509 disclose methods and materials for eliminating interfering species; however in the preferred embodiments any suitable method or material can be employed.

In another embodiment, the interference domain 48 includes a thin membrane that is designed to limit diffusion of species, for example, those greater than 34 kD in molecular weight, for example. The interference domain permits analytes and other substances (for example, hydrogen peroxide) that are to be measured by the electrodes to pass through, while preventing passage of other substances, such as potentially interfering substances. In one embodiment, the interference domain 48 is constructed of polyurethane. In an alternative embodiment, the interference domain 48 comprises a high oxygen soluble polymer, such as described above.

In preferred embodiments, the thickness of the interference domain is from about 0.1 microns or less to about 10 microns or more. In more preferred embodiments, the thickness of the interference domain is between about 0.2, 0.3, 0.4, or 0.5 microns and about 5, 6, 7, 8, or 9 microns. In more preferred embodiments, the thickness of the interference domain is from about 0.6, 0.7, 0.8, 0.9, or 1 micron to about 2, 3, or 4 microns.

Electrolyte Domain

An electrolyte domain 50 is situated more proximal to the electrochemically reactive surfaces than the interference domain 48. To ensure the electrochemical reaction, the electrolyte domain 30 includes a semipermeable coating that maintains hydrophilicity at the electrochemically reactive surfaces of the sensor interface. The electrolyte domain 50 enhances the stability of the interference domain 48 by protecting and supporting the material that makes up the interference domain. The electrolyte domain also 50 assists in stabilizing the operation of the device by overcoming electrode start-up problems and drifting problems caused by inadequate electrolyte. The buffered electrolyte solution contained in the electrolyte domain also protects against pH-mediated damage that can result from the formation of a large pH gradient between the substantially hydrophobic interference domain and the electrodes due to the electrochemical activity of the electrodes. In some embodiments, the electrolyte domain may not be used, for example, when an interference domain is not provided.

In one embodiment, the electrolyte domain 50 includes a flexible, water-swellable, substantially solid gel-like film having a "dry film" thickness of from about 2.5 microns to about 12.5 microns, more preferably from about 3, 3.5, 4, 4.5, 5, or 5.5 to about 6, 6.5, 7, 7.5, 8, 8.5, 9, 9.5, 10, 10.5, 11, 11.5, or 12 microns. "Dry film" thickness refers to the thickness of a cured film cast from a coating formulation onto the surface of the membrane by standard coating techniques.

In some embodiments, the electrolyte domain 50 is formed of a curable mixture of a urethane polymer and a hydrophilic polymer. Particularly preferred coatings are formed of a polyurethane polymer having anionic carboxylate functional groups and non-ionic hydrophilic polyether segments, which is crosslinked in the presence of polyvinylpyrrolidone and cured at a moderate temperature of about 50° C. In some preferred embodiments, the electrolyte domain 50 is formed from high oxygen soluble materials such as polymers formed from silicone, fluorocarbons, perfluorocarbons, or the like.

In one preferred embodiment, the electrolyte domain 50 is formed from a high oxygen soluble material, such as described above. In preferred embodiments, the thickness of the electrolyte domain is from about 1 micron or less to about 40, 50, 60, 70, 80, 90, or 100 microns or more. In more preferred embodiments, the thickness of the electrolyte domain is from about 2, 3, 4, or 5 microns to about 15, 20, 25, or 30 microns. In even more preferred embodiments, the thickness of the electrolyte domain is from about 6, 7, or 8 microns to about 9, 10, 11, or 12 microns.

Underlying the electrolyte domain is an electrolyte phase is a free-fluid phase including a solution containing at least one compound, typically a soluble chloride salt, which conducts electric current. In one embodiment wherein the membrane system is used with a glucose sensor such as is described herein, the electrolyte phase flows over the electrodes and is in contact with the electrolyte domain. The devices of the preferred embodiments contemplate the use of any suitable electrolyte solution, including standard, commercially available solutions. Generally, the electrolyte phase can have the same osmotic pressure or a lower osmotic pressure than the sample being analyzed. In preferred embodiments, the electrolyte phase comprises normal saline.

In various embodiments, any of these domains can be omitted, altered, substituted for, and/or incorporated together without departing from the spirit of the preferred embodiments. For example, a distinct cell impermeable domain may not exist. In such embodiments, other domains accomplish the function of the cell impermeable domain. As another example, the interference domain can be eliminated in certain embodiments wherein two-electrode differential measurements are employed to eliminate interference, for example, one electrode being sensitive to glucose and electrooxidizable interferants and the other only to interferants, such as is described in U.S. Pat. No. 6,514,718. In such embodiments, the interference domain can be omitted.

A variety of configurations are contemplated with the membrane systems of the preferred embodiments, however the exemplary configurations are not meant to be limiting and may be modified within the scope of the preferred embodiments. In one embodiment, the enzyme domain is formed from a material with a high oxygen solubility, which is believed to optimize oxygen availability to the enzyme immobilized therein. In another embodiment, all domains between the fluid supply (for example, interstitial fluid) and the enzyme (up to and including the enzyme domain) are formed from a material with a high oxygen solubility, which is believed to dynamically retain a substantially continuous path of high oxygen availability to the enzyme and/or electroactive surfaces during local ischemic periods. In yet another embodiment, all domains of a membrane system are formed from high oxygen soluble materials; in this way, the membrane system transports and/or maintains high oxygen availability substantially continuously across the membrane system, from the interstitial fluid to the implantable device surface, providing increased oxygen availability to the implantable device, for example electroactive surfaces thereon or transplanted cells located therein. While not wishing to be bound by theory, it is believed that maintaining high oxygen availability at the interface of the implantable device improves device performance even during transient ischemia and other low oxygen situations.

Reference is now made to FIGS. 5A and 5B, which are schematic diagrams of oxygen concentration profiles through a prior art membrane (FIG. 5A) and a membrane system of the preferred embodiments (FIG. 5B). FIG. 5A illustrates a fluid source 52, such as interstitial fluid within the subcutaneous space, which provides fluid to a membrane system 54a. The membrane system 54a is a conventional membrane, for example, formed from a polyurethane-based or other non-high oxygen soluble material. An oxygen-utilizing source 56, such as the immobilized enzyme within the enzyme domain 46 or electroactive surfaces 16 described herein, utilizes oxygen from the fluid as a catalyst or in an electrochemical reaction. In some alternative embodiments, the oxygen-utilizing source 56 comprises cells within a cell transplantation device, which utilize oxygen in the fluid for cellular processes.

The upper dashed lines represent oxygen concentration in the fluid source ($C_f$) and oxygen concentration in the membrane system ($C_m$) at equilibrium (namely, without oxygen utilization) under normal conditions. However, when the membrane system 54a interfaces with an oxygen-utilizing source 56, oxygen concentration within the membrane system will be utilized. Accordingly, line 58a represents oxygen concentration under normal conditions decreasing at steady state as it passes through the membrane system 54a to the oxygen-utilizing source 56. While not wishing to be bound by theory, the oxygen concentration at the interface between the membrane system 54a and the oxygen-utilizing source 56 provides sufficient oxygen under normal conditions for oxygen-utilizing sources in vivo, such as enzymatic reactions, cellular processes, and electroactive surfaces.

Unfortunately, "normal conditions" do not always occur in vivo, for example during transient ischemic periods, such as described in more detail above with reference to FIG. 3. During "ischemic conditions," oxygen concentration is decreased below normal to a concentration as low as zero. Accordingly, line 60a represents oxygen concentration during an ischemic period, wherein the oxygen concentration of the fluid source ($C_f$) is approximately half of its normal concentration. A linear relationship exists between the fluid source oxygen concentration ($C_f$) and the membrane system oxygen concentration ($C_m$) (see Hitchman, M. L. Measurement of Dissolved Oxygen. In *Chemical Analysis*; Elving, P., Winefordner, J., Eds.; John Wiley & Sons: New York, 1978; Vol. 49, pp. 63-70). Accordingly, line 62a represents the oxygen concentration within the membrane system during the ischemic period, which is approximately half of its normal concentration. Unfortunately, the resulting oxygen concentration at the interface of the membrane 54a and oxygen-utilizing source 56 is approximately zero. While not wishing to bound by any particular theory, it is believed that the oxygen concentration at the interface between the conventional membrane system 54a and the oxygen-utilizing source 56 does not provide sufficient oxygen for oxygen-utilizing sources in vivo, such as enzymatic reactions, cellular processes, and electroactive surfaces, during some ischemic conditions.

Referring to FIG. 5B, a fluid source 52, such as interstitial fluid within the subcutaneous space, provides fluid to a membrane system 54b. The membrane system 54b is a membrane system of the preferred embodiments, such as an enzyme domain 46 or an entire membrane system formed from a high oxygen soluble material such as described herein, through which the fluid passes. An oxygen-utilizing source 56, such as the immobilized enzyme described herein, utilizes oxygen from the fluid as a catalyst. In some alternative embodiments, the oxygen-utilizing source 56 comprises cells within a cell transplantation device, which utilize oxygen in the fluid for cellular processes. In some alternative embodiments, the oxygen-utilizing source 56 comprises an electroactive surface that utilizes oxygen in an electrochemical reaction.

The upper dashed lines represent oxygen concentration in the fluid source ($C_f$) and oxygen concentration in the membrane system ($C_m$) at equilibrium (namely, without oxygen utilization) under normal conditions. The membrane system of the preferred embodiments 54b is illustrated with a significantly higher oxygen concentration than the conventional membrane 54a. This higher oxygen concentration at equilibrium is attributed to higher oxygen solubility inherent in the properties of the membrane systems of the preferred embodiments as compared to conventional membrane materials. Line 58b represents oxygen concentration under normal conditions decreasing at steady state as it passes through the membrane system 54b to the oxygen-utilizing source 56. While not wishing to be bound by theory, the oxygen concentration at the interface between the membrane system 54b and the oxygen-utilizing source 56 is believe to provide sufficient oxygen under normal conditions for oxygen-utilizing sources in vivo, such as enzymatic reactions, cellular processes, and electroactive surfaces.

Such as described above, "normal conditions" do not always occur in vivo, for example during transient ischemic periods, wherein oxygen concentration is decreased below normal to a concentration as low as zero. Accordingly, line 60b represents oxygen concentration during ischemic conditions, wherein the oxygen concentration of the fluid source ($C_f$) is approximately half of its normal concentration. Because of the linear relationship between the fluid source oxygen concentration ($C_f$) and the membrane system oxygen concentration ($C_m$), the membrane system oxygen concentration, which is represented by a line 62b, is approximately half of its normal concentration. In contrast to the conventional membrane 62a illustrated in FIG. 5A, however, the high oxygen solubility of the membrane system of the preferred embodiments dynamically retains a higher oxygen availability within the membrane 54b, which can be utilized during ischemic periods to compensate for oxygen deficiency, illustrated by sufficient oxygen concentration 62b provided at the interface of the membrane 54b and oxygen-utilizing source 56. Therefore, the high oxygen solubility of the membrane systems of the preferred embodiments enables device function even during transient ischemic periods.

Methods and devices that are suitable for use in conjunction with aspects of the preferred embodiments are disclosed in co-pending U.S. patent application Ser. No. 10/842,716, filed May 10, 2004 and published as U.S. Application Publication No. 2005-0031689 and entitled, "MEMBRANE SYSTEMS INCORPORATING BIOACTIVE AGENTS"; co-pending U.S. patent application Ser. No. 10/838,912 filed May 3, 2004 and published as U.S. Application Publication No. 2005-0245799 and entitled, "IMPLANTABLE ANALYTE SENSOR"; U.S. patent application Ser. No. 10/789,359 filed Feb. 26, 2004 and published as U.S. Application Publication No. 2005-0192557 and entitled, "INTEGRATED DELIVERY DEVICE FOR A CONTINUOUS GLUCOSE SENSOR"; U.S. application Ser. No. 10/695,636 filed Oct. 28, 2003 and published as U.S. Application Publication No. 2005-0090607 and entitled, "SILICONE COMPOSITION FOR BIOCOMPATIBLE MEMBRANE"; U.S. application Ser. No. 10/648,849 and published as U.S. Application Publication No. 2005-0043598 filed Aug. 22, 2003 and entitled, "SYSTEMS AND METHODS FOR REPLACING SIGNAL ARTIFACTS IN A GLUCOSE SENSOR DATA STREAM"; U.S. application Ser. No. 10/646,333 filed Aug. 22, 2003 and published as U.S. Application Publication No. 2004-0199059 and entitled, "OPTIMIZED SENSOR GEOMETRY FOR AN IMPLANTABLE GLUCOSE SENSOR"; U.S. application Ser. No. 10/647,065 filed Aug. 22, 2003 and published as U.S. Application Publication No. 2005-0112169 entitled, "POROUS MEMBRANES FOR USE WITH IMPLANTABLE DEVICES"; U.S. application Ser. No. 10/633,367 filed Aug. 1, 2003 and published as U.S. Application Publication No. 2005-0027463 and entitled, "SYSTEM AND METHODS FOR PROCESSING ANALYTE SENSOR DATA"; U.S. Pat. No. 6,702,857 entitled "MEMBRANE FOR USE WITH IMPLANTABLE DEVICES"; U.S. application Ser. No. 09/916,711 filed Jul. 27, 2001 and published as U.S. Application Publication No. 2003-0032874 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and published as U.S. Application Publication No. 2003-0217966 and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000 and issued as U.S. Pat. No. 6,741,877 and entitled "DEVICE AND METHOD FOR DETERMINING ANALYTE LEVELS"; U.S. application Ser. No. 09/636,369 filed Aug. 11, 2000 and issued as U.S. Pat. No. 6,558,321 and entitled "SYSTEMS AND METHODS FOR REMOTE MONITORING AND MODULATION OF MEDICAL DEVICES"; and U.S. application Ser. No. 09/916,858 filed Jul. 27, 2001 and issued as U.S. Pat. No. 6,862,465 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE"; U.S. Appl. No. 60/489,615 filed Jul. 23, 2003 and entitled "ROLLED ELECTRODE ARRAY AND ITS METHOD FOR MANUFACTURE"; U.S. Appl. No. 60/490,010 filed Jul. 25, 2003 and entitled "INCREASING BIAS FOR OXYGEN PRODUCTION IN AN ELECTRODE ASSEMBLY"; U.S. Appl. No. 60/490,208 filed Jul. 25, 2003 and entitled "ELECTRODE ASSEMBLY WITH INCREASED OXYGEN GENERATION"; U.S. Appl. No. 60/490,007 filed Jul. 25, 2003 and entitled "OXYGEN-GENERATING ELECTRODE FOR USE IN ELECTROCHEMICAL SENSORS"; U.S. application Ser. No. 10/896,637 filed on Jul. 21, 2004 and published as U.S. Application Publication No. 2005-0051427 and entitled "ROLLED ELECTRODE ARRAY AND ITS METHOD FOR MANUFACTURE"; U.S. application Ser. No. 10/896,772 filed on Jul. 21, 2004 and published as U.S. Application Publication No. 2005-0056552 and entitled "INCREASING BIAS FOR OXYGEN PRODUCTION IN AN ELECTRODE ASSEMBLY"; U.S. application Ser. No. 10/897,377 filed on Jul. 21, 2004 and published as U.S. Application Publication No. 2005-0051440 and entitled "ELECTROCHEMICAL SENSORS INCLUDING ELECTRODE SYSTEMS WITH INCREASED OXYGEN GENERATION"; U.S. application Ser. No. 10/89,7312 filed on Jul. 21, 2004 and published as U.S. Application Publication No. 2005-0115832 and entitled "ELECTRODE SYSTEMS FOR ELECTROCHEMICAL SENSORS". The foregoing patent applications and patents are incorporated herein by reference in their entireties.

All references cited herein are incorporated herein by reference in their entireties. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. An electrochemical glucose sensor for determining a presence or a concentration of glucose in a fluid, the sensor comprising:
    a multilayer membrane system comprising a cell impermeable domain that is substantially impermeable to cells, a resistance domain configured to restrict a flow of the glucose therethrough, and an enzyme domain comprising an enzyme that reacts with the glucose in the fluid as it passes though the enzyme domain; and
    a working electrode comprising a conductive material, wherein the working electrode is configured to measure a product of a reaction of the enzyme with the glucose,
    wherein the enzyme domain, the resistance domain, and the cell impermeable domain each comprise a polymer material with a higher oxygen solubility than an oxyhydrocarbon polymer and wherein each of the enzyme domain, the resistance domain, and the cell impermeable domain is configured to be permeable to the glucose.

2. The electrochemical sensor of claim 1, wherein the polymer material is selected from the group consisting of silicone, fluorocarbon, and perfluorocarbon.

3. The electrochemical sensor of claim 1, wherein the resistance domain comprises a polymer material selected from the group consisting of silicone, fluorocarbon, and perfluorocarbon.

4. The electrochemical sensor of claim 1, wherein the cell impermeable domain comprises a polymer material selected from the group consisting of silicone, fluorocarbon, and perfluorocarbon.

5. The electrochemical sensor of claim 1, further comprising a cell disruptive domain that comprises a substantially porous structure, wherein the cell disruptive domain is located more distal to the working electrode than the enzyme domain, and wherein the cell disruptive domain comprises a polymer material with high oxygen solubility.

6. The electrochemical sensor of claim 5, wherein the cell disruptive domain comprises a polymer material selected from the group consisting of silicone, fluorocarbon, and perfluorocarbon.

7. The electrochemical sensor of claim 1, further comprising an interference domain configured to limit or block interfering species, wherein the interference domain is located more proximal to the working electrode than the enzyme domain, and wherein the interference domain comprises a polymer material with a high oxygen solubility.

8. The electrochemical sensor of claim 7, wherein the interference domain comprises a polymer material selected from the group consisting of silicone, fluorocarbon, and perfluorocarbon.

9. The electrochemical sensor of claim 1, further comprising an electrolyte domain configured to provide hydrophilicity at the working electrode, wherein the electrolyte domain is located more proximal to the working electrode than the enzyme domain, and wherein the electrolyte domain comprises a polymer material with a high oxygen solubility.

10. The electrochemical sensor of claim 9, wherein the electrolyte domain comprises a polymer material selected from the group consisting of silicone, fluorocarbon, and perfluorocarbon.

11. The electrochemical sensor of claim 1, wherein the polymer material has a higher oxygen solubility than hydrocarbonaceous polymers.

12. The electrochemical sensor of claim 1, wherein the polymer material has an oxygen permeability of at least about 50 Barrer.

13. The electrochemical sensor of claim 1, wherein the polymer material has an oxygen permeability of at least about 100 Barrer.

14. The electrochemical sensor of claim 1, wherein the polymer material has an oxygen permeability of at least about 500 Barrer.

15. An electrochemical glucose sensor for determining a presence or a concentration of glucose in a fluid, the glucose sensor comprising:
    a membrane system comprising:
        an enzyme domain comprising an enzyme that reacts with the glucose in the fluid as it passes through the enzyme domain; and
        a resistance domain configured to partially restrict a flow of the glucose therethrough, wherein the resistance domain is located more distal to the working electrode than the enzyme domain;
        a cell impermeable domain that is substantially impermeable to cells; and
    a working electrode, wherein the working electrode is configured to measure a product of a reaction of the enzyme with the glucose,
    wherein the resistance domain and the cell impermeable domain each comprise a silicone polymer blended with a hydrophilic polymer and are configured to be at least partially permeable to the glucose.

16. The electrochemical sensor of claim 15, further comprising a cell disruptive domain that comprises a substantially porous structure configured to allow tissue ingrowth, wherein the cell disruptive domain is located more distal to the working electrode than the cell impermeable domain, and wherein the cell disruptive domain comprises a polymer material with high oxygen solubility.

17. The electrochemical sensor of claim 16, wherein the cell disruptive domain comprises a polymer material selected from the group consisting of silicone, fluorocarbon, and perfluorocarbon.

18. The electrochemical sensor of claim 15, wherein the silicone polymer blended with the hydrophilic polymer has a higher oxygen solubility than hydrocarbonaceous polymers.

19. The electrochemical sensor of claim 15, wherein the silicone polymer blended with the hydrophilic polymer has an oxygen permeability of at least about 50 Barrer.

20. The electrochemical sensor of claim 15, wherein the silicone polymer blended with the hydrophilic polymer has an oxygen permeability of at least about 100 Barrer.

21. The electrochemical sensor of claim 15, wherein the silicone polymer blended with the hydrophilic polymer has an oxygen permeability of at least about 500 Barrer.

* * * * *

UNITED STATES PATENT AND TRADEMARK OFFICE
CERTIFICATE OF CORRECTION

PATENT NO. : 7,379,765 B2  Page 1 of 1
APPLICATION NO. : 10/896639
DATED : May 27, 2008
INVENTOR(S) : Petisce et al.

It is certified that error appears in the above-identified patent and that said Letters Patent is hereby corrected as shown below:

At column 4, line 5, please delete "acylcamitine" and insert -- acylcarnitine --, therefore.

At column 4, line 25, please delete "diptheria" and insert -- diphtheria --, therefore.

At column 4, line 32, please delete "perioxidase" and insert -- peroxidase --, therefore.

At column 22, line 31, please delete "10/89,7312" and insert -- 10/897,312 --, therefore.

At column 23, line 12, in claim 1 please delete "though" and insert -- through --, therefore.

Signed and Sealed this

Twenty-fifth Day of November, 2008

JON W. DUDAS
*Director of the United States Patent and Trademark Office*